United States Patent
Griffiths et al.

(10) Patent No.: US 11,536,730 B2
(45) Date of Patent: *Dec. 27, 2022

(54) METHODS FOR DIAGNOSING MOTOR NEURON DISEASES

(71) Applicant: SWANSEA UNIVERSITY, Swansea (GB)

(72) Inventors: William Griffiths, West Glamorgan (GB); Peter Crick, West Glamorgan (GB); Yuqin Wang, West Glamorgan (GB); Jens Kuhle, West Glamorgan (GB); Andreas Sailer, West Glamorgan (GB); Juan Zhang, West Glamorgan (GB); Martin Turner, West Glamorgan (GB)

(73) Assignee: Swansea University, Swansea (GB)

( * ) Notice: Subject to any disclaimer, the term of this patent is extended or adjusted under 35 U.S.C. 154(b) by 108 days.

This patent is subject to a terminal disclaimer.

(21) Appl. No.: 16/315,118

(22) PCT Filed: Jul. 4, 2017

(86) PCT No.: PCT/GB2017/051971
§ 371 (c)(1),
(2) Date: Jan. 3, 2019

(87) PCT Pub. No.: WO2018/007803
PCT Pub. Date: Jan. 11, 2018

(65) Prior Publication Data
US 2019/0310267 A1    Oct. 10, 2019

(30) Foreign Application Priority Data
Jul. 4, 2016 (GB) .................................. 1611636

(51) Int. Cl.
*G01N 33/68* (2006.01)
*G01N 33/92* (2006.01)
*G01N 33/50* (2006.01)

(52) U.S. Cl.
CPC ......... *G01N 33/6896* (2013.01); *G01N 33/92* (2013.01); *G01N 33/5088* (2013.01); *G01N 2800/28* (2013.01); *G01N 2800/52* (2013.01)

(58) Field of Classification Search
None
See application file for complete search history.

(56) References Cited

U.S. PATENT DOCUMENTS

2013/0178375 A1* 7/2013 Kassis .................. C12Q 1/6876
506/7
2015/0233953 A1   8/2015 Griffiths et al.

FOREIGN PATENT DOCUMENTS

WO    2014131836 A2    9/2014
WO    2014132052 A2    9/2014

OTHER PUBLICATIONS

Crick, P J., et al. Quantitative Charge-Tags for Sterol and Oxysterol Analysis, Clinic Chemistry, 61(2), 400-411. (Year: 2015).*

(Continued)

*Primary Examiner* — Xiaoyun R Xu
(74) *Attorney, Agent, or Firm* — Dorsey & Whitney LLP

(57) ABSTRACT

The invention relates to methods for determining whether a subject is afflicted with a motor neuron disease, the method comprising conducting an analysis of cerebrospinal fluid and/or plasma, measuring the level of one or more sterol/oxysterol analytes, and comparing these to reference values. Further, the invention relates to methods of identifying agents suitable for the treatment of MND, and monitoring the progress of the disease.

19 Claims, 5 Drawing Sheets

(56) References Cited

OTHER PUBLICATIONS

IPRP issued in International Application No. PCT/GB2017/051971 dated Jan. 17, 2019.
Abdel-Khalik J. et al.: "Defective cholesterol metabolism in amyotrophic lateral sclerosis", J. Lip. Res., vol. 58, No. 1, Nov. 3, 2016 (Nov. 3, 2016), pp. 267-278, XP055396828.
Karu K. et al.: "Nano-liquid chromatographytandem mass spectrometry analysis of oxysterols in brain: monitoring of cholesterol autoxidation", Chem. Phys. Lipids, vol. 164, No. 6, May 6, 2011 (May 6, 2011), pp. 411-424, XP028262802.
Kim S.-M. et al.: "Amyotrophic lateral sclerosis is associated with hypolipidemia at the presymptomatic stage in mice", PLOS ONE, vol. 6, No. 3, E17985, Mar. 25, 2011 (Mar. 25, 2011), pp. 1-5, XP055397158.
La Marca V. et al.: "Lecithin-cholesterol acyltransferase in brain: Does oxidative stress influence the 24-hydroxycholesterol esterification?", Neurosci. Res., vol. 105, Oct. 9, 2015 (Oct. 9, 2015), pp. 19-27, XP029519091.
Theofilopoulos S. et al.: "Cholestenoic acids regulate motor neuron survival via liver X receptors", J. Clin. Invest., vol. 124, No. 11, Oct. 1, 2014 (Oct. 1, 2014), pp. 4829-4842, XP055396834.
International Search Report and Written Opinion received in PCT International Application No. PCT/GB2017/051971, dated Aug. 10, 2017.

* cited by examiner

METHODS FOR DIAGNOSING MOTOR NEURON DISEASES

RELATED APPLICATIONS

This application is a United States National Stage entry of PCT/GB2017/051971, filed Jul. 4, 2017 and entitled "METHODS FOR DIAGNOSING MOTOR NEURON DISEASES," which claims priority to United Kingdom Patent Application No. 1611636.0, filed on Jul. 4, 2016, each of which is incorporated by reference in its entirety.

The present invention relates to methods for the diagnosis or prognosis of motor neuron disease, including amyotrophic lateral sclerosis (ALS) and related conditions.

BACKGROUND OF THE INVENTION

Motor neuron diseases (MND) belong to a group of neurological disorders attributed to the destruction of motor neurons of the central nervous system and degeneration of the motor neuron pathway. Such diseases differ from other neurodegenerative diseases including Parkinson's disease and Alzheimer's disease, which are caused by the destruction of neurons other than motor neurons. Typically, MNDs are progressive, degenerative disorders that affect upper and lower motor neurons, leading to successive global muscular denervation. Generally, MNDs strike in middle age, although a wide age range of onset can be observed, spanning from age 18 to 85. Symptoms include difficulty swallowing, limb weakness, slurred speech, impaired gait, facial weakness and muscle cramps. The cause(s) of most MNDs are not known, but environmental, toxic, viral or genetic factors are all suspects.

Amyotrophic lateral sclerosis (ALS) is the most common type of MND. It is a fatal motor neuron disease characterized by a loss of pyramidal cells in the cerebral motor cortex (i.e., giant Betz cells), anterior spinal motor neurons and brain stem motor neurons, and degeneration thereof into pyramidal cells. ALS shows, from a clinical aspect, both upper motor neurons and lower motor neurons signs, and shows rapid clinical deterioration after onset of the disease, thus leading to death within a few years. It is a progressive neuromuscular disease characterized by motor neuron death and skeletal muscle atrophy. 95% of patients die from respiratory failure, usually within 3-5 years after the onset of symptoms. The disease remains incurable. Riluzole is approved for the treatment of the condition by the United States Food and Drug Administration; however, it extends patient life span by only a few months, and does not relieve symptoms.

Edvaradone (5-methyl-2-phenyl-4H-pyrazol-3-one) is presently under study as a treatment for ALS.

Edvaradone

About 5-10% of ALS cases are inherited, or "familial" (FALS); the majority ALS cases are referred to as "sporadic" (SALS), occurring seemingly at random with no clearly identified risk factors. Presently, diagnostic methods to determine ALS in patients are primarily based on the symptoms that the patient exhibits, combined with a battery of tests to rule out other pathologies.

Both SALS and FALS manifest similar pathological and clinical phenotypes, suggesting that different initiating molecular insults promote a similar neurodegenerative process. Many cases of FALS (20-25%) are associated with mutations in the Cu/Zn superoxide dismutase gene (SOD1). Transgenic mice (G93) harboring human ALS-causing SOD1 mutations recapitulate the neuronal and muscle impairment of human ALS patients and thus these mice are expensively used to investigate the pathomechanisms of ALS and trial new therapeutics.

Metabolic biomarkers that could definitively identify the presence or absence of MND, and in particular ALS, in a symptomatic patient are urgently needed. Further, there are no known effective therapeutic regimes. A method of identifying agents suitable for the treatment of MND remains extremely desirable.

SUMMARY OF THE INVENTION

In a first embodiment, the invention provides a method for determining whether a subject suspected of having a motor neuron disease (MND) is afflicted with MND, the method comprising:
(a) obtaining a sample of cerebrospinal fluid from the subject;
(b) subjecting the sample to analysis to determine the concentration in the sample of at least one of a steroid selected from cholesterol (1), desmosterol (2), or combinations thereof, and optionally an additional oxysterol;
(c) comparing the concentration of the at least one steroid present in the sample to a reference value of the at least one steroid obtained from a control population consisting of individuals not afflicted with MND; and
(d) diagnosing the subject as afflicted with MND if the concentration of the at least one steroid from the subject is greater than the reference value.

In a second embodiment, the invention provides an in vitro method for determining whether a subject suspected of having motor neuron disease (MND) is afflicted with MND, the method comprising:
(a) subjecting a sample of cerebrospinal fluid to analysis to determine the concentration in the sample of at least one of a steroid selected from cholesterol (1), desmosterol (2), or combinations thereof, and optionally an additional oxysterol;
(b) comparing the concentration of the at least one steroid present in the sample to a reference value of the at least one steroid obtained from a control population consisting of individuals not afflicted with MND; and
(c) diagnosing the subject as afflicted with MND if the concentration of the at least one steroid from the subject is greater than the reference value.

In a third embodiment, the invention provides a method for determining whether a subject suspected of having motor neuron disease (MND) is afflicted with MND, the method comprising:
(a) obtaining a sample of cerebrospinal fluid from the subject;
(b) subjecting the sample to analysis to determine the concentration in the sample of at least one of one oxysterol selected from the group consisting of 3β,7α-dihydroxycholest-5-en-26-oic acid (3β,7α-diHCA), 3β-hydroxycholest-5-en-26-oic acid (3β-HCA), 3β,7β-Dihydroxycholest-5-en-26-oic acid (3β,7β-diHCA), 7α-hydroxy-3-oxocholest-4-en-26-oic acid (7αH,3O-CA), (25R)26-hydroxycholesterol (26-HC), Cholest-5-ene-3β,24S-diol (24-S HC), 7α,25-Dihydroxycholest-4-en-3-one (7α-25-diHCO), 7α,26-Dihydroxycholest-4-en-3-one (7α-26-diHCO), 7α,24-Dihydroxy-3-oxocholest-4-en-26-oic acid (7α,24-diH, 3O-CA), 7α,25-Dihydroxy-3-oxocholest-4-en-26-oic acid (7α,25-diH, 3O-CA), 7α-Hydroxy-26-norcholest-4-ene-3,24-dione (7α-H,26-nor-C3,24-diO), 7α-Hydroxy-3,24-bisoxocholest-4-en-26-oic acid (7αH,3,24-diO-CA) 7α-hydroxy-3-oxochol-4-enoic acid (7αH,3O-Δ⁴-BA, (5)), 7-oxocholesterol (7O-C, (6)) and 7α-hydroxycholest-4-en-3-one (7α-HCO, (7)) or combinations thereof;
(c) comparing the concentration of the at least one oxysterol present in the sample to a reference value of the at least one oxysterol obtained from a control population consisting of individuals not afflicted with MND; and
(d) diagnosing the subject as afflicted with MND if the concentration of the at least one oxysterol from the subject is lower than the reference value.

In a fourth embodiment, the invention provides a method for determining whether a subject suspected of having motor neuron disease (MND) is afflicted with MND, the method comprising:
(a) obtaining a sample of cerebrospinal fluid from the subject;
(b) subjecting the sample to analysis to determine the concentration in the sample of at least one of one oxysterol selected from the group consisting of 7α-hydroxy-3-oxochol-4-enoic acid (7αH,3O-Δ⁴-BA, (5))
(c) comparing the concentration of the at least one oxysterol present in the sample to a reference value of the at least one oxysterol obtained from a control population consisting of individuals not afflicted with MND; and
(d) diagnosing the subject as afflicted with MND if the concentration of the at least one oxysterol from the subject is higher than the reference value.

In a fifth embodiment, the invention provides an in vitro method for determining whether a subject suspected of having motor neuron disease (MND) is afflicted with MND, the method comprising:
(a) subjecting a sample of plasma from the subject to analysis to determine the concentration in the sample of at least one of one oxysterol selected from 7α-hydroxy-3-oxochol-4-enoic acid (7αH,3O-Δ⁴-BA, (5)), 7-oxocholesterol (7O-C, (6)), 3β-hydroxycholest-5-en-26-oic acid (3β-HCA), (25R)26-hydroxycholesterol (26-HC), and 7α-hydroxycholest-4-en-3-one (7α-HCO, (7)) or combinations thereof;
(b) comparing the concentration of the at least one oxysterol present in the sample to a reference value of the at least one oxysterol obtained from a control population consisting of individuals not afflicted with MND; and
(c) diagnosing the subject as afflicted with MND if the concentration of the at least one oxysterol from the subject is lower than the reference value.

In a sixth embodiment, the invention provides a method of identifying an agent for the treatment of a MND, the method comprising:
(a) administering a candidate agent to a non-human mammal model of a MND;
(b) obtaining a sample of cerebrospinal fluid from the non-human mammal;
(c) subjecting the sample to analysis to determine the concentration in the sample of at least one of a steroid selected from cholesterol (1), desmosterol (2), or combinations thereof, and optionally an additional oxysterol;
(d) comparing the concentration of the at least one steroid present in the sample to a reference value of the at least one steroid obtained from a control population consisting of individuals not afflicted with MND; and
(e) identifying the candidate agent as an agent for the treatment of a MND if the concentration of the at least one steroid from the subject is decreased compared to the value prior to administration.

In a seventh embodiment, the invention provides a method for determining the responsiveness of a subject having a motor neuron disease (MND) to treatment with at least one MND therapy, the method comprising
(a) administering the at least one MND therapy to a subject having a MND;
(b) obtaining a sample of cerebrospinal fluid from the subject;
(c) (subjecting the sample to analysis to determine the concentration in the sample of at least one of a steroid selected from cholesterol (1), desmosterol (2), or combinations thereof, and optionally an additional oxysterol;
(d) comparing the concentration of the at least one steroid present in the sample to the level of the same steroid or steroids prior to administration of the therapy; wherein an increase in the concentration of the at least one steroid is indicative that the subject is responsive or is likely to respond to the therapy.

In an eighth embodiment, the invention provides an in vitro method for determining whether a subject suspected of having motor neuron disease (MND) is afflicted with MND, the method comprising:
(a) subjecting a sample of plasma from the subject to analysis to determine the concentration in the sample of cholest-5-ene-3b,7α,25-triol (7α,25-diHC);
(b) comparing the concentration of cholest-5-ene-3b,7α,25-triol (7α,25-diHC) present in the sample to a reference value of the at least one oxysterol obtained from a control population consisting of individuals not afflicted with MND; and
(c) diagnosing the subject as afflicted with MND if the concentration of the at least one oxysterol from the subject is lower than the reference value.

In a ninth embodiment, the invention provides an in vitro method for determining whether a subject suspected of having motor neuron disease (MND) is afflicted with MND, the method comprising:
(a) subjecting a sample of plasma from the subject to analysis to determine the concentration in the sample of 7α,25-Dihydroxycholest-4-en-3-one (7α-25-diHCO):
(b) comparing the concentration of 7α,25-Dihydroxycholest-4-en-3-one (7α-25-diHCO) present in the sample to a reference value of the at least one oxysterol obtained from a control population consisting of individuals not afflicted with MND; and
(c) diagnosing the subject as afflicted with MND if the concentration of the at least one oxysterol from the subject is greater than the reference value.

DRAWINGS

Figure 3:
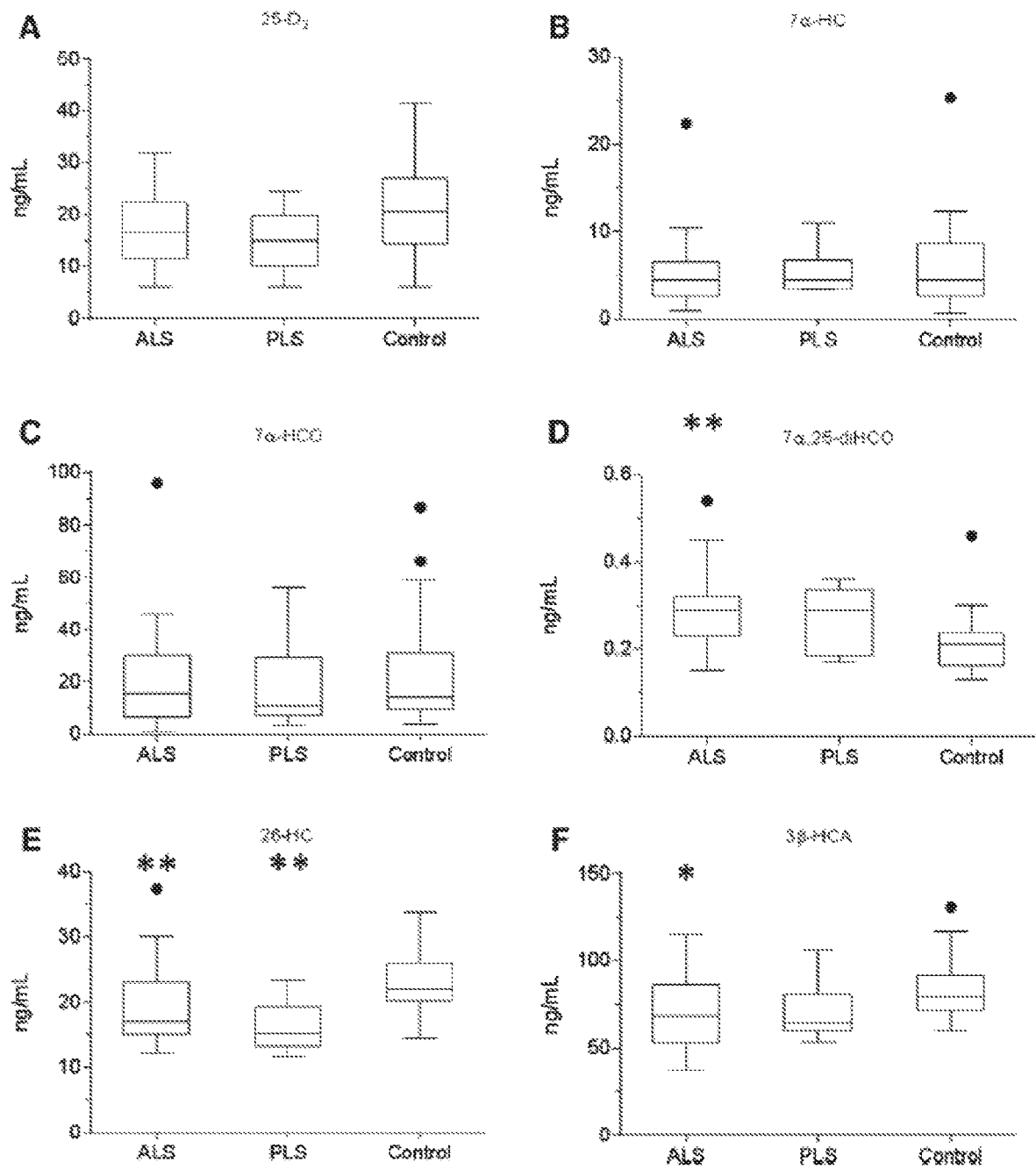

FIG. 3 is a series of graphs of 25-hydroxycholecalciferol 25-D$_3$ and cholesterol metabolites in serum. Box and whiskers plots showing the concentrations (ng/ml) of 25-hydroxycholecalciferol 25-D$_3$ (A), 7α-HC (B), 7α-HCO (C), 7α,25-diHCO (D), 26-HC (E), and 3β-HCA (F) in serum from ALS (n=35) and PLS (n=6) patients and healthy controls (n=24). The bottom and top of the box are the first and third quartiles, and the band inside the box represents the median. The whiskers extend to the most extreme data points, which are no more than 1.5 times the range between first and third quartile distant from the box. Points beyond that are plotted individually.

Figure 4:
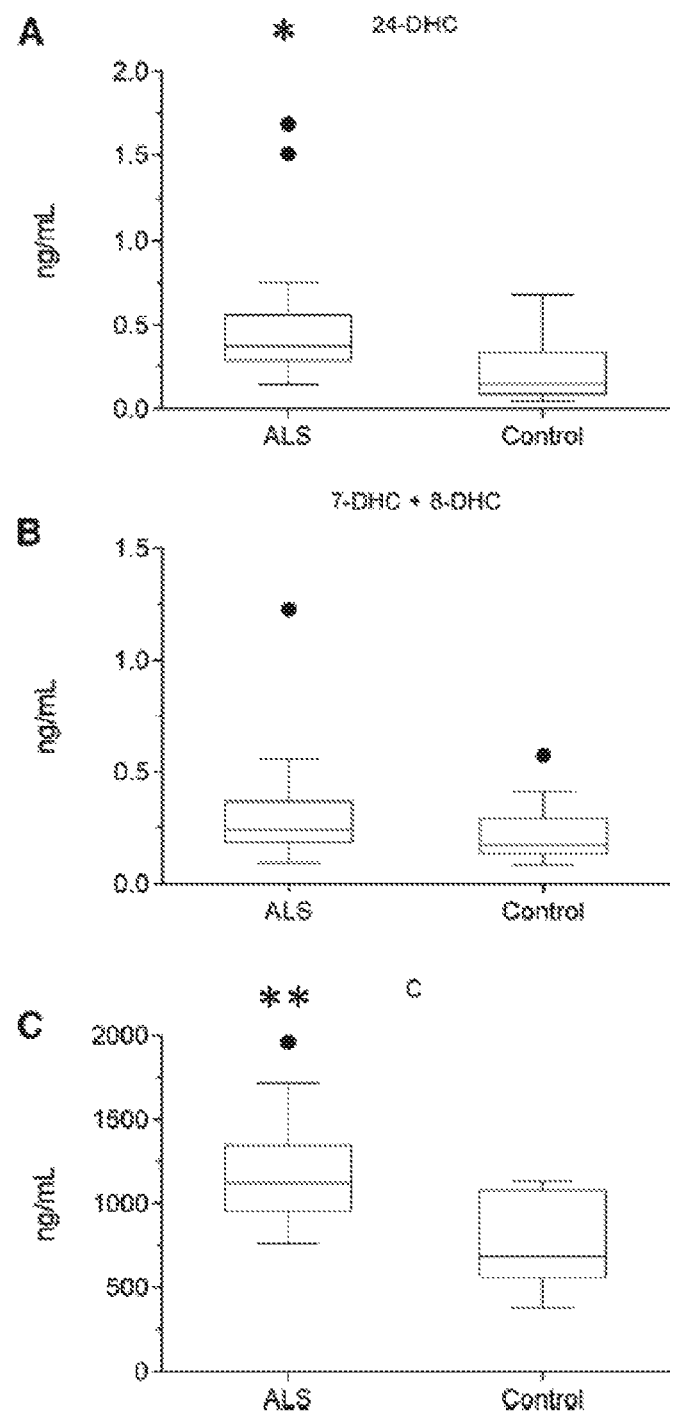

FIG. 4 is a series of graphs showing the concentration of cholesterol and its precursors in CSF. Box and whisker plots showing concentrations (ng/ml) of 24-DHC (A), 7-DHC 8-DHC (B), and cholesterol (C) in CSF from ALS (n=20) patients and healthy controls (n=15).

Figure 5:
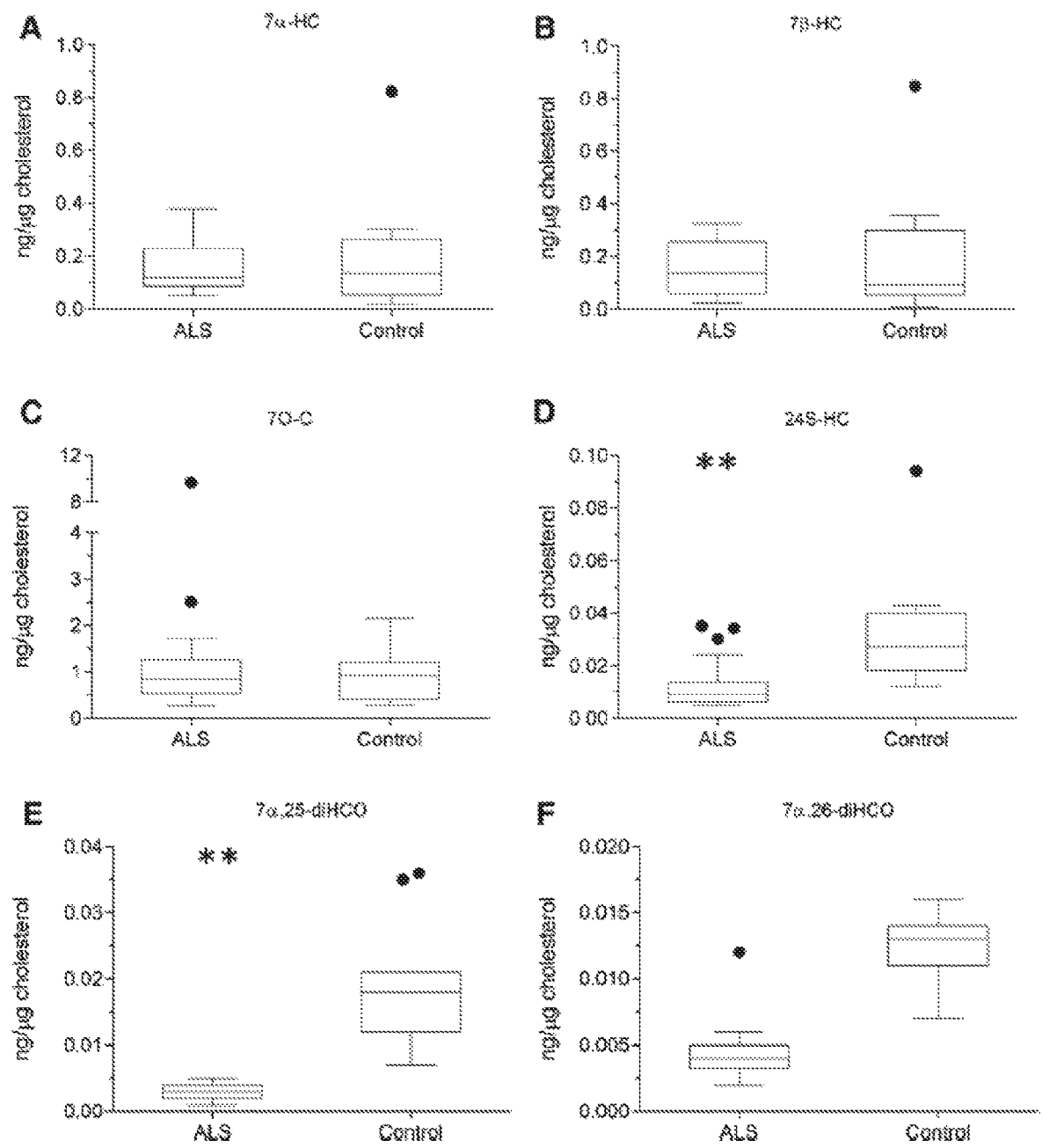

FIG. 5 is a series of graphs showing the concentration of CYP7A1, CYP46A1 and CH25H pathway metabolites in CSF. Box and whisker plots showing concentrations (ng/μg cholesterol) of 7α-HC (A), 7β-HC (B), 7O-C (C), 24S-HC (D), 7α,25-diHCO (E), and 7α,26-diHCO (F) in CSF from ALS (n=20) patients and healthy controls (n=15).

Figure 6:
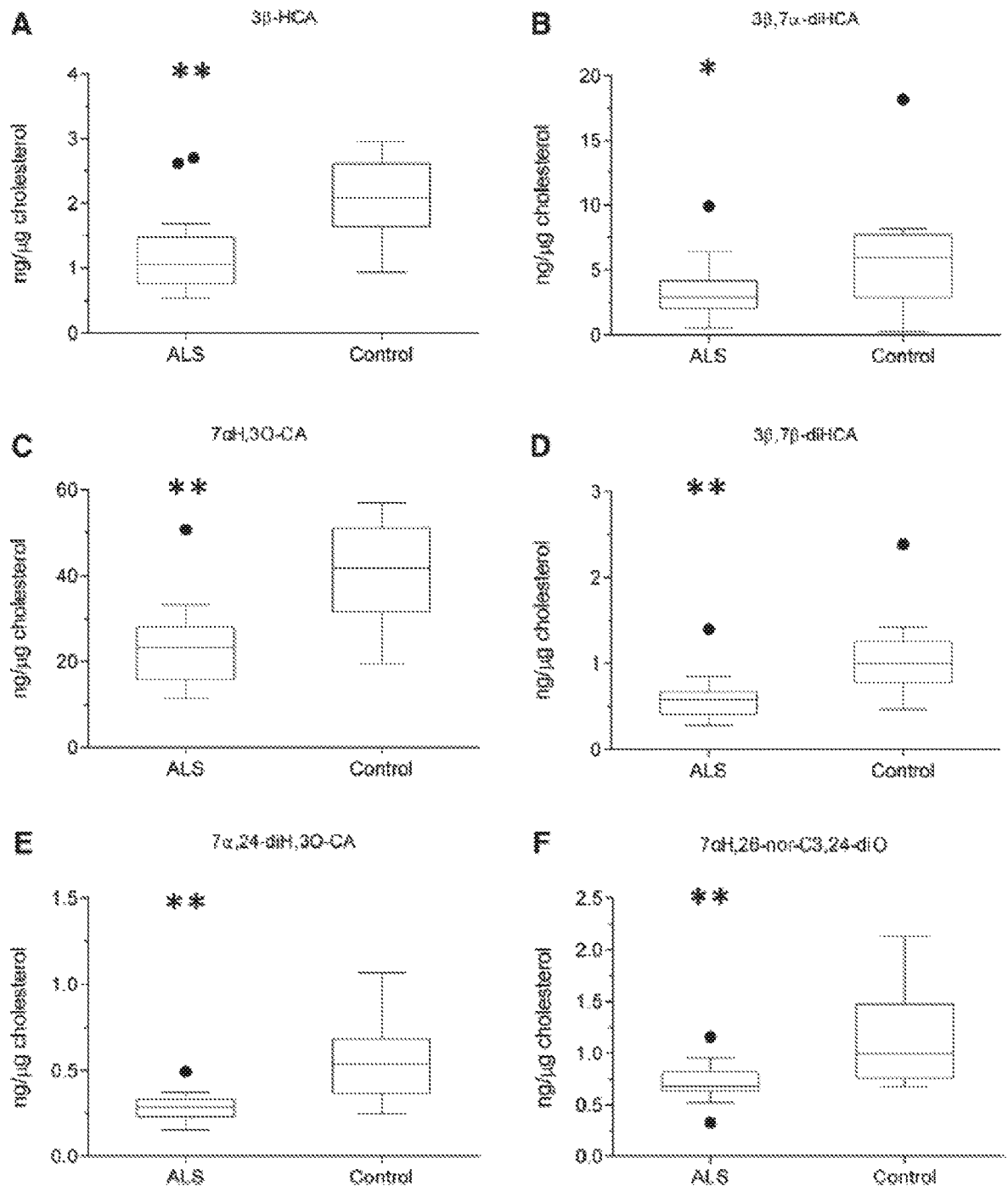

FIG. 6 is a series of graphs showing the concentration of acidic pathway metabolites in CSF. Box and whisker plots showing concentrations (ng/μg cholesterol) of 3β-HCA (A), 3β,7α-diHCA (B), 7αH,3O-CA (C), 3β,7β-diHCA (D), 7α,24-diH, 3O-CA (E), and 7αH,26-nor-C-3,24-diO (F) in CSF from ALS (n=20) patients and healthy controls (n=15).

DETAILED DESCRIPTION OF THE INVENTION

Perturbation of sterol and cholesterol pathways have recently been linked to various immune disorders. Oxysterols, oxidised metabolites of cholesterol or its precursors, are key mediators of these pathways. As well as being essential metabolites controlling cholesterol levels and leading to the production of bile acids, oxysterols have been shown to modulate the immune system. They, and their down-stream metabolites, are ligands for nuclear hormone receptors such as the liver X receptors (LXRs), the farnesoid X receptor (FXR), the pregnane X receptor (PXR), the RAR-related orphan receptor γt (RORc2) (19-22), they modulate transcription in macrophages, and RORc2 activation plays a central role in the differentiation of Th17 cells.

The inventors determined sterol and oxysterol concentrations under pathophysiological conditions and determined using liquid chromatography-mass spectrometry (lc-ms) oxysterol levels in plasma and cerebrospinal fluid (CSF) from patients suffering from motor neuron disease (MND) and control patients (CP).

The present disclosure relates to the finding that one or more of a set of sterols and/or oxysterols may be used as a biomarker for screening, diagnosing, or monitoring disorders involving accumulation of one or more sterols and/or oxysterols such as various types of motor neuron disease, including amyotrophic lateral sclerosis (ALS), primary lateral sclerosis, progressive muscular atrophy, progressive bulbar palsy and pseudobulbar palsy.

In particular, the invention relates to elevated levels of cholesterol (1) and its immediate precursor desmosterol (2) in cerebrospinal fluid in patients suffering from motor neuron disease.

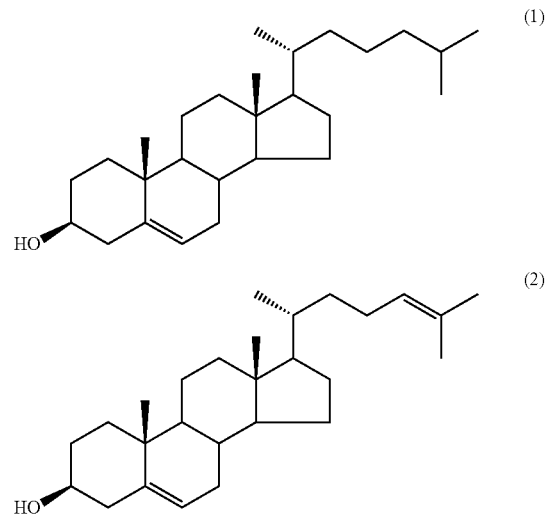

Oxysterols are commonly referred to as oxidized derivatives of cholesterol, typically generated non-enzymatically, enzymatically as a normal part of cholesterol metabolism, or absorbed through dietary intake. Oxysterols typically have a hydroxyl-, epoxy- or a keto-group on the cholesterol molecule. In some embodiments of the present disclosure, the oxysterol can be any one or more of 7α-hydroxy-3-oxo-cholest-4-enoic acid (7αH,3O-CA, (3)), 7α,(25R)26-dihydroxycholest-4-en-3-one, (7α,(25R)26-diHCO (4)), 7α-hydroxy-3-oxochol-4-enoic acid (7αH,3O-Δ$^4$-BA, (5)), 7-oxocholesterol (7O-C, (6)), 7α-hydroxycholest-4-en-3-one (7α-HCO, (7)), 3β,7α-dihydroxycholest-5-en-26-oic acid (3β,7α-diHCA), 3β-hydroxycholest-5-en-26-oic acid (3β-HCA), 3β,7β-Dihydroxycholest-5-en-26-oic acid (3β,7β-diHCA), 7α-hydroxy-3-oxocholest-4-en-26-oic acid (7αH,3O-CA), (25R)26-hydroxycholesterol (26-HC), Cholest-5-ene-3β,24S-diol (24-S HC), 7α,25-Dihydroxycholest-4-en-3-one (7α-25-diHCO), 7α,26-Dihydroxycholest-4-en-3-one (7α-26-diHCO), 7α,24-Dihydroxy-3-oxocholest-4-en-26-oic acid (7α,24-diH, 3O-CA), 7α-Hydroxy-26-nor-cholest-4-ene-3,24-dione (7α-H,26-nor-C3,24-diO), 7α-Hydroxy-3,24-bisoxocholest-4-en-26-oic acid (7αH,3,24-diO-CA)

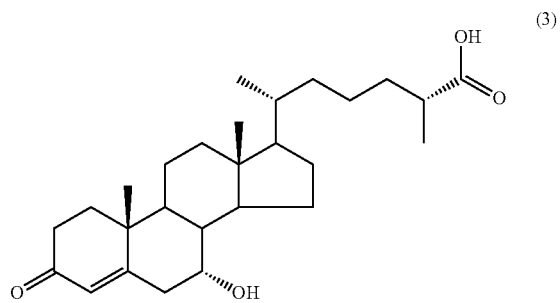

-continued

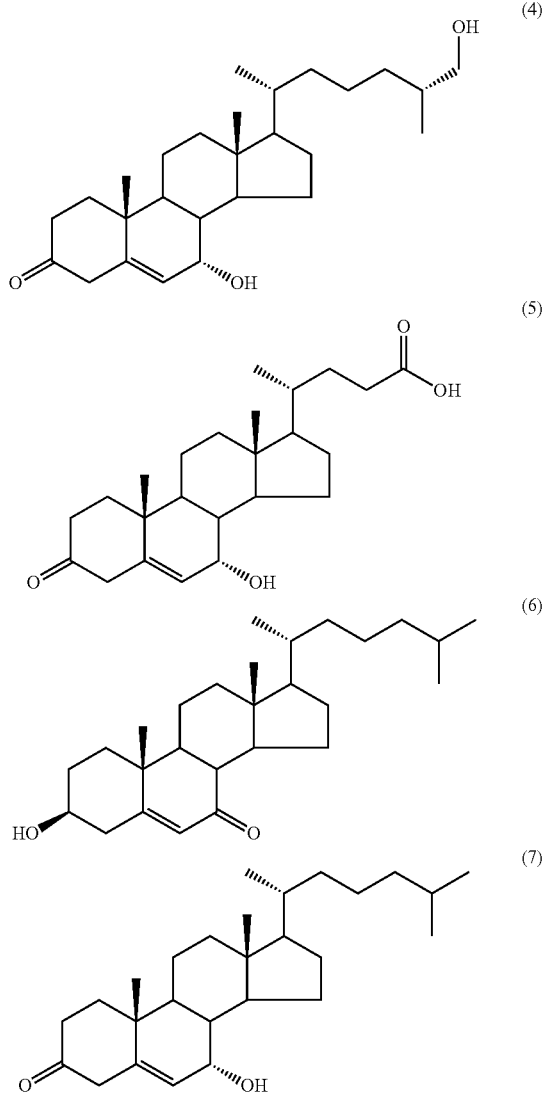

An oxysterol may be present in a subject at a level that is elevated compared to the level of the sterol/oxysterol in a population not afflicted with a disorder involving accumulation of one or more oxysterols such as amyotrophic lateral sclerosis, primary lateral sclerosis, progressive muscular atrophy, progressive bulbar palsy and pseudobulbar palsy. Certain sterols/oxysterols can be present at levels below those found in control populations, and/or at levels that vary over time. Levels of sterols/oxysterols can be used for screening, diagnosing, and/or monitoring disorders involving accumulation of one or more oxysterols such as amyotrophic lateral sclerosis, primary lateral sclerosis, progressive muscular atrophy, progressive bulbar palsy and pseudobulbar palsy. Additionally, levels of sterols/oxysterols can be used to assess the efficacy of candidate agents as therapies for a MND, for example in transgenic animal models for MND.

In particular, in patients suffering from MND, the cerebrospinal fluid shows differences in cholesterol metabolite concentrations compared to controls and also in the concentration of cholesterol (1) and desmosterol (2), which are increased. The concentration of 7α,(25R)26-dihydroxycholest-4-en-3-one (7α,(25R)26-diHCO (4)), is also reduced as is its downstream metabolite, 7αH,3O-CA (3). Levels of one or more of 3β,7α-dihydroxycholest-5-en-26-oic acid (3β,7α-diHCA), 3β-hydroxycholest-5-en-26-oic acid (3β-HCA), 3β,7β-Dihydroxycholest-5-en-26-oic acid (3β,7β-diHCA), 7α-hydroxy-3-oxocholest-4-en-26-oic acid (7αH,3O-CA), (25R)26-hydroxycholesterol (26-HC), Cholest-5-ene-3β,24S-diol (24-S HC), 7α,25-Dihydroxycholest-4-en-3-one (7α-25-diHCO), 7α,26-Dihydroxycholest-4-en-3-one (7α-26-diHCO), 7α,24-Dihydroxy-3-oxocholest-4-en-26-oic acid (7α,24-diH, 3O-CA), 7α-Hydroxy-26-nor-cholest-4-ene-3,24-dione (7α-H,26-nor-C3,24-diO), 7α-Hydroxy-3,24-bisoxocholest-4-en-26-oic acid (7αH,3,24-diO-CA) are also reduced. On the other hand, levels of 7α-Hydroxy-3-oxochol-4-en-24-oic acid (7αH,3O-Δ⁴-BA) are increased.

Additionally, patients suffering from MND display decreased levels of certain oxysterols in plasma. In particular, levels of 7α-hydroxy-3-oxochol-4-enoic acid (7αH,3O-Δ$^4$-BA, (5)), 7-oxocholesterol (7O-C, (6)) 7α-hydroxycholest-4-en-3-one (7α-HCO, (7)), 3β-hydroxycholest-5-en-26-oic acid (3β-HCA), and (25R)26-hydroxycholesterol (26-HC) are decreased relative to control samples. On the other hand, levels of 7α,25-Dihydroxycholest-4-en-3-one (7α-25-diHCO) are increased.

The present disclosure provides methods for identifying a subject having, or at risk of developing, motor neuron disease by detecting an altered concentration of one or more sterols/oxysterols in a biological sample collected from the subject. The present disclosure provides methods for screening or diagnosing subjects (including infants and neonatal subjects) for MND. Also disclosed are methods for monitoring the progression, remission, and clinical status of MND and for evaluating the efficacy of therapeutic treatment of MND.

In some embodiments, the invention relates strictly to in vitro methods of diagnosis. In such embodiments, the invention excludes methods of diagnosis practised on the human or animal body. In these embodiments, the analysis is conducted on samples (such as plasma or cerebrospinal fluid) which are collected previously.

Methods for Quantifying Oxysterol Concentration in Biological Samples

As used herein, a chromatography procedure or combination of chromatography procedures can be used to quantify the sterol/oxysterol concentration in a biological sample. Methods for isolating sterols, including cholesterol, its precursor and oxysterols are known in the art. In some embodiments, the quantification step of the method of identifying a subject with MND can include: determining the relative concentration of the sterol/oxysterol and internal standard in the biological sample by correlating the area under the curve obtained for the known amount of oxysterol internal standard with the area under the curve obtained for the one or more oxysterols. Suitable internal standards are known in the art; the preferred standards are 24R/S-[25,26,26,26,27,27,27-$^2$H$_7$]hydroxycholesterol, 7α,25-[26,26,26,27,27,27-$^2$H$_6$]dihydroxycholesterol, 22R-[25,26,26,26,27,27,27-$^2$H$_7$]hydroxycholest-4-en-3-one ([$^2$H$_7$]22R-HCO), and [25,26,26,26,27,27,27-$^2$H$_7$]cholesterol.

In some embodiments, the sterol/oxysterol quantification methodology may be compatible with existing screening assays and may be adaptable to automation and high throughput screening. Methods useful to determine the concentration of one or more sterols/oxysterols in a biological sample indicative of MND may be carried out using any suitable methodology or combination of methodologies that detects the presence or absence of sterols/oxysterols, and preferably, methodologies which determine their concentration.

Suitable methods for determining the concentration of sterols and oxysterols include chromatographic methods, preferably high performance liquid chromatography, liquid chromatography-mass spectrometry (LC-MS), gas chromatography-mass spectrometry (GC-MS), time-of-flight mass spectrometry (TOF-MS), tandem mass spectrometry ("TMS"), matrix assisted laser desorption ionization-mass spectrometry (MALDI-MS), and electrospray ionization-tandem mass spectrometry (ESI-TMS), and thin layer chromatography (TLC). Of these, LC-MS is preferred.

Optionally, and preferably, a derivatization step may be used prior to the step of determining the concentration of sterols/oxysterols in the biological sample. Derivatization methods are known in the art, e.g. from WO2014/037725, incorporated herein in its entirety. Disclosed are charge tagging hydrazine derivatives having the formulae in Table 1; * adjacent to a C atom represents $^{13}C$ and * adjacent to a N atom indicates $^{15}N$, X represents halide (fluoride, chloride, or bromide). Of these, (i) (Girard P reagent) is preferred.

TABLE 1

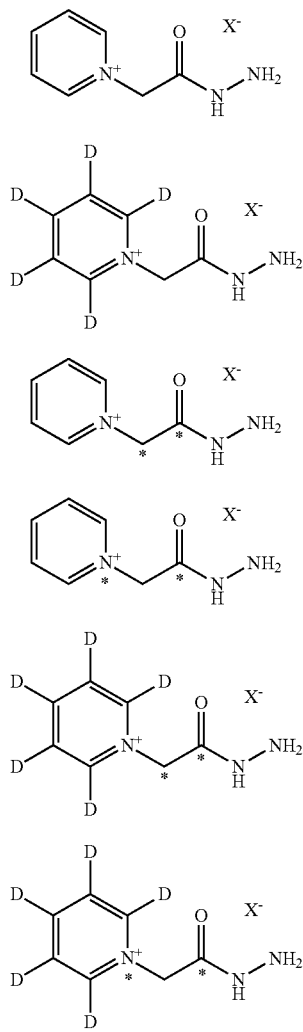

TABLE 1-continued

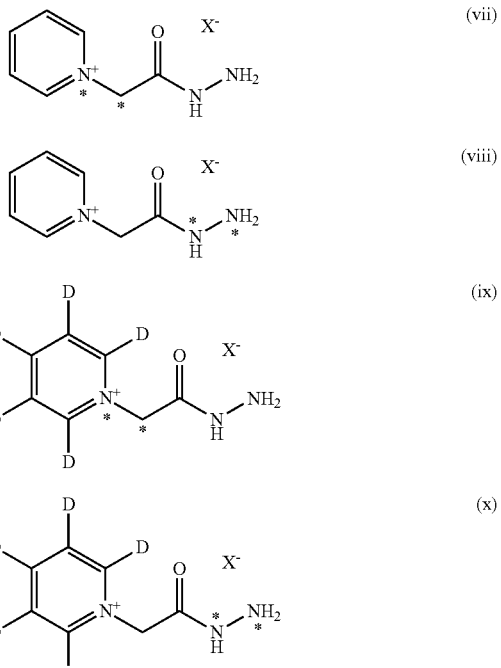

The hydrazine derivatives in table 1 react with carbonyl groups present in sterols and oxysterols to form hydrazones. Although some steroids possess a carbonyl group readily available for derivatisation via coupling to a hydrazine group e.g. 7-oxocholesterol (7O-C, (6)), most oxysterols do not. However, many steroids have an OH group at the steroid 3-position which can be oxidised to give a ketone. Some embodiments of the invention include a step of reaction with an agent or mixture of agents capable of oxidising 3-hydroxy groups in steroid compounds. In some embodiments it is preferred that the oxidising agent is selective for the steroid 3-position.

Suitable oxidising agents include enzymatic agents such as a cholesterol oxidase or a cholesterol dehydrogenase enzyme. Suitable cholesterol oxidase enzymes capable of effecting the conversion of 3-hydroxy groups to 3-ketones can be obtained from *Streptomyces* species (MacLachlan et al., 2000).

Derivatization with other classes of reagents is also contemplated. Suitable derivatives include trimethylsilyl (TMS) ethers, TMS ether methyl esters, bis picolinyl esters, bis nicotinyl esters, N,N-dimethylglycyl esters, and O-3-trimethylammonium-propyl) oximes. The use of such agents is known in the art.

One method of LC-MS analysis exploits reversed phase LC on a Hypersil Gold C18 column (50×2.1 mm, 1.9 μm particle size) with a methanol/acetonitrile/0.1% formic acid gradient and detection with a ion trap-Orbitrap hybrid high resolution mass spectrometer. Analyte identification is achieved by using exact mass, measured in the high resolution Orbitrap, and by multiple stage fragmentation (MSn) in the ion trap. A significant advantage of GP derivatisation is that the derivatised oxysterols give distinct fragmentation patterns allowing isomer differentiation. A further advantage is that the method is applicable to down-stream metabolites of oxysterols including cholestenoic and cholenoic acids. The sensitivity of the method allows oxysterols to be detected at the ng/mL level from 100 μL of plasma and the 30 pg/mL level from 250 μL of CSF. It is also applicable to vitamins D analysis [100].

Several alternative methods of measuring levels of cholesterol are known in the art, and in certain embodiments, are applicable to the methods of the invention. Various methods have been devised to measure cholesterol in fluids. Such methods include the Abell-Levy-Brodie-Kendall (ALBK) saponification method is a precise method (*J Biol Chem* 1952; 195:357-366), the cholesterol ester hydrolase-cholesterol oxidase-peroxidase (CEH-CO-POD) chromogenic method (*Clin Chem* 1974; 20:470-475), and enzymatic procedures using NAD(P1)-specific cholesterol dehydrogenase (CDH).

In some embodiments, the "level" or "concentration" of an analyte (e.g. an oxysterol) refers to the concentration expressed in nanograms per millilitre. However, sometimes it is appropriate to express the level normalised to that of cholesterol, i.e. in terms of ng of oxysterol per μg of cholesterol.

Screening and Diagnosing Methods.

In some embodiments of the present disclosure, a method for identifying a subject having, or at risk of developing, a MND is provided. The method preferably comprises quantifying or determining the concentration of one or more sterols and/or oxysterols in a biological sample obtained from the subject. The concentration of the one or more sterols and/or oxysterols in the tested biological sample collected from the subject can be compared with a reference value. Detection and quantification of elevated concentration(s) of one or more of the sterol/oxysterol(s) in the biological sample as compared to a reference value (which may be a predetermined value) can presumptively identify the subject as having, or at risk for developing, MND.

In some embodiments, the present disclosure provides a method for identifying a subject having, or at risk of developing, MND by an increased concentration of one or more oxysterols in a biological sample collected from the subject. According to some of these embodiments, steps for identifying a subject having MND comprise: (a) obtaining a sample of cerebrospinal fluid from the subject; (b) quantifying the concentration of sterols/oxysterols comprising cholesterol (1), desmosterol (2), 7αH,3O-CA (3) 7α,(25R)26-diHCO (4), 3β,7α-dihydroxycholest-5-en-26-oic acid (3β,7α-diHCA), 3β-hydroxycholest-5-en-26-oic acid (3β-HCA), 3β,7β-Dihydroxycholest-5-en-26-oic acid (3β,7β-diHCA), 7α-hydroxy-3-oxocholest-4-en-26-oic acid (7αH,3O-CA), (25R)26-hydroxycholesterol (26-HC), Cholest-5-ene-3β,24S-diol (24-S HC), 7α,25-Dihydroxycholest-4-en-3-one (7α-25-diHCO), 7α,26-Dihydroxycholest-4-en-3-one (7α-26-diHCO), 7α,24-Dihydroxy-3-oxocholest-4-en-26-oic acid (7α,24-diH, 3O-CA), 7α-Hydroxy-26-nor-cholest-4-ene-3,24-dione (7α-H,26-nor-C3,24-diO), 7α-Hydroxy-3,24-bisoxocholest-4-en-26-oic acid (7αH,3,24-diO-CA), 7-oxocholesterol (7O-C, (6)) or 7α-hydroxycholest-4-en-3-one (7α-HCO, (7)) or combinations thereof; and (c) comparing the concentration of the sterol(s)/oxysterol(s) present in the cerebrospinal fluid to a reference value obtained from a control population, wherein if the concentration of the sterol(s)/oxysterol(s) from the subject is lower than the reference value, the subject can be identified as having, or at risk for developing, MND. Diagnosis of MND may also be confirmed using the methods of these embodiments.

In some embodiments, the present disclosure provides a method for identifying a subject having, or at risk of developing, MND by an increased concentration of one or more oxysterols in a biological sample collected from the subject. According to some of these embodiments, steps for identifying a subject having MND comprise: (a) obtaining a sample of cerebrospinal fluid from the subject; (b) quantifying the concentration of sterols/oxysterols comprising 7α-hydroxy-3-oxochol-4-enoic acid (7αH,3O-Δ$^4$-BA, (5)); and (c) comparing the concentration of the sterol(s)/oxysterol(s) present in the cerebrospinal fluid to a reference value obtained from a control population, wherein if the concentration of the sterol(s)/oxysterol(s) from the subject is higher than the reference value, the subject can be identified as having, or at risk for developing, MND. Diagnosis of MND may also be confirmed using the methods of these embodiments.

According to further embodiments, steps for identifying a subject having MND comprise: (a) obtaining a sample of plasma from the subject; (b) quantifying the concentration of oxysterols comprising 3β-HCA, 26-HC, 7αH,3O-Δ$^4$-BA, (5), 7O-C, (6) and 7α-HCO, (7) or combinations thereof; and (c) comparing the concentration of the oxysterol(s) present in the plasma to a reference value obtained from a control population, wherein if the concentration of the oxysterol(s) from the subject is lower than the reference value, the subject can be identified as having, or at risk for developing, MND.

According to further embodiments, steps for identifying a subject having MND comprise: (a) obtaining a sample of plasma from the subject; (b) quantifying the concentration of oxysterols comprising 7α-25-diHCO; and (c) comparing the concentration of the oxysterol(s) present in the plasma to a reference value obtained from a control population, wherein if the concentration of the oxysterol(s) from the subject is higher than the reference value, the subject can be identified as having, or at risk for developing, MND.

Combinations of the above embodiments are also contemplated, namely comparing the levels of both sterols/oxysterols in cerebrospinal fluid with levels of thereof sterols/oxysterols or combinations thereof in plasma with reference levels, and identifying on that basis the subject as having, or at risk for developing, MND.

The methods of the invention can be used to differentiate subjects suffering from MND with those suffering from other diseases with similar symptoms. These include benign cramp fasciculation syndrome, cervical radiculomyelopathy (multilevel degenerative disease of the cervical spine), multifocal motor neuropathy with conduction block, inclusion body myositis, diabetic amyotrophy, Guillain-Barré syndrome, post-polio syndrome, myasthenia gravis or Lambert-Eaton myasthenic syndrome, peripheral nerve lesions, thyrotoxicosis with associated myopathy, spinal cord tumours, cerebrovascular disease and stroke, polymyositis or dermatomyositis, glioma of brainstem, HIV-associated neuropathy/myopathy/radiculopathy (as one of the complications of HIV), lepto-meningeal disease, Lyme disease, spinal muscular atrophy (Kennedy's syndrome), hereditary polyneuropathies—eg, Charcot-Marie-Tooth syndrome, focal muscular atrophies (monomelic amyotrophy), post-radiation myeloplexopathy, viral plexopathies, and Tay-Sachs disease.

Reference Levels

A reference level is a level of sterol/oxysterol concentration to which the level of a sterol/oxysterol of interest in a sample is compared.

In some embodiments, the reference level for each sterol/oxysterol can be based on known concentrations in healthy and diseased populations. The reference or control levels may be set as appropriate for the subject being screened. In other embodiments, the oxysterol levels identified in a subject can be compared with a matched unselected, population. In some embodiments, the subject can be compared with a matched population of unaffected (i.e., healthy) subjects and/or a matched population of affected subjects. In some embodiments, the control population can be a matched control population wherein the control population is matched to the subject by gender and/or age.

In a preferred embodiment, subjects that have cerebrospinal fluid levels of one or more of cholesterol (1), desmosterol (2), 7αH,3O-CA (3) or 7α,(25R)26-diHCO (4), having values above about the 70th percentile, 75th percentile, 80th percentile, 90th percentile, 95th percentile, 96th percentile, 97th percentile, 98th percentile, 99th percentile, or higher, as compared with an appropriate control population may be diagnosed as suffering from MND.

The level of one or more of cholesterol (1), desmosterol (2), 7αH,3O-CA (3) or 7α,(25R)26-diHCO (4) is preferably at least 1.1 times, more preferably at least 1.2 times, more preferably at least 1.5 times, more preferably at least double, the level of the compound found in a sample taken from healthy subjects, who are not suffering from MND. These levels may be determined empirically or by comparison with a previously determined standard levels.

In an alternative embodiment, subjects that have plasma levels of one or more of 7αH,3O-$\Delta^4$-BA, (5), 7O-C, (6) and 7α-HCO, (7), having values below about the 30th percentile, 25th percentile, 20th percentile, 10th percentile, 5th percentile, 4th percentile, 3rd percentile, 2nd percentile, 1st percentile, or lower, as compared with an appropriate control population may be diagnosed as suffering from MND.

The level of one or more of 7αH,3O-$\Delta^4$-BA, (5), 7O-C, (6) and 7α-HCO, (7) is preferably less than 0.75 times, more preferably less than half, the level of the compound found in a sample taken from healthy subjects, who are not suffering from MND. These levels may be determined empirically or by comparison with a previously determined standard levels.

The invention provides methods for monitoring the progression of a subject that has been diagnosed with MND. Thus, increasing levels of cholesterol (1), desmosterol (2), 7α,(25R)26-diHCO (4) and/or 7αH,3O-$\Delta$4-BA, (5), in cerebrospinal fluid, and/or decreasing levels of 7O-C, (6) 7α-HCO, (7), 3β-HCA, and/or 26-HC in plasma may be used to track the clinical progression of MND. In one embodiment, the efficacy of a treatment can be assessed using the methods disclosed herein.

In one embodiment, wherein cholesterol levels are analysed, a subject may be determined as having motor neuron disease if the level of cholesterol is higher than 1000 ng/mL, more preferably higher than 1100 ng/mL, more preferably higher than 1200 ng/mL, more preferably higher than 1300 ng/mL, more preferably higher than 1400 ng/mL, most preferably higher than 1500 ng/mL.

In one embodiment, wherein desmosterol levels are analysed, a subject may be determined as having motor neuron disease if the level of desmosterol is higher than 0.2 ng/mL, more preferably higher than 0.3 ng/mL, more preferably higher than 0.4 ng/mL, more preferably higher than 0.5 ng/mL, more preferably higher than 0.6 ng/mL, most preferably higher than 0.7 ng/mL.

EXPERIMENTAL SECTION

Example 1

Samples of plasma and cerebrospinal fluid were obtained from patients suffering from ALS and from a control population.

Assay for Sterols Including Oxysterols, Cholestenoic and Cholenoic Acids

Non-esterified sterols in plasma were assayed by lc-ms exploiting enzyme-assisted derivatisation utilising the Girard P reagent (GP) (Crick P J, William B T, Abdel-Khalik J et al. (2015) Clin Chem 61: 400-11. Griffiths W J, Crick P J, Wang Y et. al. (2013) Free Radic Biol Med 59: 69-84.

Plasma (100 µL) was added dropwise to a solution of absolute ethanol (1.05 mL) containing 24R/S-[25,26,26,26, 27,27,27-2H7]hydroxycholesterol ([2H7]24-OHC) and 22R-[25,26,26,26,27,27,27-2H7]hydroxycholest-4-en-3-one ([2H7]22R-OHCO]) (20 ng of each in 1.05 mL of absolute ethanol) in an ultrasonic bath. After 5 min the solution was diluted to 70% ethanol by addition of 0.35 mL of water, ultrasonicated for a further 5 min and centrifuged at 14,000×g at 4° C. for 30 min. The supernatant was loaded onto a 200 mg Certified Sep-Pak C18 cartridge (pre-conditioned with 4 mL of absolute ethanol followed by 6 mL 70% ethanol) and allowed to flow at ~0.25 mL/min. The flow-through was combined with a column wash of 70% ethanol (5.5 mL) to give SPE1-Fr1 containing the oxysterols. A second fraction (SPE1-Fr2) was collected by eluting with a further 4 mL of 70% ethanol before elution 5 of cholesterol, 7-dehydrocholesterol and similarly hydrophobic sterols using 2 mL of absolute ethanol (SPE1-Fr3).

Charge Tagging of Sterols and Oxysterols from Plasma

The sterol and oxysterol fractions (A) from above were re-constituted in 100 µL of propan-2-ol then treated with KH2PO4 buffer (1 mL 50 mM, pH 7) containing 3 µL of cholesterol oxidase (2 mg/mL in H$_2$O, 44 units/mg protein). The reaction mixture was incubated at 37° C. for 1 hr then quenched with 2.0 mL of methanol. Glacial acetic acid (150 was added followed by Girard P (GP) reagent (190 mg bromide salt or 150 mg chloride salt, 0.80 mmol). The mixture was vortexed then incubated at room temperature overnight in the dark. To remove excess reagent from the reaction mixture a recycling method was used. A 200 mg Certified Sep-Pak C18 cartridge was preconditioned with methanol (6 mL), 10% methanol (6 mL) and finally 70% methanol (4 mL). The derivatization mixture from above (3.25 mL in ~70% organic) was applied to the column and allowed to flow through at ~0.25 mL/min. The column was washed with 70% methanol (1 mL) followed by 35% methanol (1 mL) and the combined eluent diluted with water (4 mL) to give a solution in 9 mL of 35% methanol. This solution was applied to the column, collected, and combined with a column wash of 17.5% methanol (1 mL). Water (9 mL) was added to give a solution in 19 mL of 17.5% methanol which was again applied to the column. The flow-through was discarded and the column washed with 10% methanol (6 mL). Derivatized sterols/oxysterols were then eluted from the column with methanol (3×1 mL, SPE2-Fr1, Fr2, Fr3) followed by absolute ethanol (1 mL, SPE2-Fr4). Cholesterol and 7-dehydrocholesterol were found to be almost exclusively present in SPE2-Fr3 while oxysterols elute in SPE2-Fr1 and Fr2. The fractions (B) were treated in an identical fashion to the (A) fractions but in the absence of cholesterol oxidase. This allows differentiation of sterols oxidised to contain an oxo group from those naturally possessing one. In later studies the 200 mg Certified Sep-Pak C18 cartridge has been replaced by an Oasis HLB 60-mg column [Crick An Bio Chem 2015].

For CSF analysis the only modifications made to the above protocol for plasma were that the volume of CSF was 250 µL cf. 100 µL plasma, the concentrations of internal standards 24R/S-[25,26,26,26,27,27,27-2H7]hydroxycholesterol, 7α,25-[26,26,26,27,27,27-2H6]dihydroxycholesterol and 22R-[25,26,26,26,27,27,27-2H7]hydroxylcholest-4-en-3-one ([2H7]22R-HCO) were 16-1.6 ng/mL CSF and [25,26,26,26,27,27,27-2H7]cholesterol was 16 µg/mL CSF and that the size of the final C18 cartridge was 50 mg cf. 100 mg with plasma.

LC-MS(MSn) on 5 the LTQ-Orbitrap

To analyse GP-tagged oxysterols, SPE2-Fr1 and -Fr2 were combined and diluted to give a final solution of 60% methanol. For each experiment, 20 µL was injected onto the LC column and MS, MS2 and MS3 spectra recorded as described below. For the analysis of the more non-polar sterols SPE2-FR1, -Fr2 and -Fr3 were combined prior to dilution to 60% methanol.

LC was performed on a Ultimate 3000 HPLC system (Dionex, Surrey, UK) using a Hypersil GOLD revered phase column (1.9 µm particle size, 50×2.1 mm, Thermo Fisher). Mobile phase A consisted of 33.3% methanol, 16.7% acetonitrile and 0.1% formic acid. Mobile phase B consisted of 63.3% methanol, 31.7% acetonitrile and 0.1% formic acid. The chromatographic run started at 20% B for 1 min before increasing the proportion of B to 80% over 7 minutes and maintaining this for a further 5 min. The proportion of B was returned to 20% over 6 s and re-equilibration was for 3 min, 54 s to give a total run time of 17 min. The flow rate was 200 µL/min and the eluent was directed to the atmospheric pressure ionization (API) source of an LTQ-Orbitrap. The Orbitrap was calibrated externally before each analytical session and the mass accuracy was better than 5 ppm.

The method consisted of a Fourier Transform (FT)-MS scan in the Orbitrap at 30,000 resolution (full width at half-maximum height; FWHM), simultaneous to which sequential MS2 or MS3 scans were carried out in the linear ion trap (LIT) with normalised collision energies of for MS2 and for MS3 (instrument settings).

Statistical Analysis

An ANOVA test was run for each sterol on linear and logarithmic scales. The log scale used a transformation log 2(+1) to avoid issues with zero and small numbers. Univariant t-tests were performed against the control group, *P<0.05; P<0.01. Concentrations given in the text are mean±standard deviation (SD). The boxplots in FIG. 1, S1 and S2** were generated with default parameters in R version 3.02. The bottom and top of the central box are the first and third quartiles, and the band inside the box is the median.

The whiskers extend to the most extreme data points which are no more than 1.5 times the range between first and third quartile distant from the box. Points beyond that are plotted individually. Pair wise correlations between plasma or CSF levels and specific analyte shown in FIG. 3 and FIG. S3 were performed by R version 3.02. Tables S3 and S4 lists P values for the significance of the correlations. The P values that are below 0.05/((21*20)/2)=0.000238 for CSF and below 0.05/((22*21)/2)=0.000216 for plasma are highlighted, these are significant after a Bonferronni correction at 5%.

The CSF from the ALS group shows differences in cholesterol metabolite concentrations compared to controls and also in the concentration of cholesterol itself (1.66±0.36 µg/mL cf. 1.24±0.33 ng/mL, P<0.01). The concentration of 7α,(25R)26-dihydroxycholest-4-en-3-one (7α,(25R)26-diHCO, 0.03±0.01 ng/mL, cf. 0.02±0.01 ng/mL, P<0.01) is increased as is its downstream metabolites 7αH,3O-CA, although not quite to the same extent (24.45±11.16 ng/mL, cf. 17.40±4.63 ng/mL, P=0.07).

Patients with ALS also show an elevation in the metabolites of the "acidic pathway" in CSF—7α,(25R)26-diHCO (P<0.01) is increased.

Example 2

Analysis of Sterols, Oxysterols, and Cholestenoic and Cholenoic Acids in Serum.

Using the method of Example 1, serum from 35 patients diagnosed with ALS (24 male, 11 female, mean age 65) and 24 control samples (12 male, 12 female, mean age 58). Six patients diagnosed with the upper motor neuron-only, very slowly progressive variant of ALS, termed PLS (2 male, 4 female, mean age 69), were separately compared with the control group. Concentrations of nonesterified cholesterol, two of its precursors, and >40 metabolites were measured.

There was no significant difference in the concentrations of cholesterol or its precursors desmosterol (24-DHC) or 7-dehydrocholesterol (7-DHC) between ALS, PLS, or control samples. Note we report here the concentration of 7-DHC as the sum of 7-DHC and its isomer 8-DHC, which are only partially resolved on our LC system. The 8-DHC is an enzymatic product of 7-DHC. Similarly, there was no significant difference in the concentration of the 7-DHC metabolite 25-hydroxyvitamin D3 (25-D3) in serum of the ALS patients compared with controls (FIG. 3).

The first steps of all cholesterol metabolism lead to hydroxycholesterol isomers, collectively known as oxysterols. A minor pathway, initiated in activated macrophages, leads to 25-hydroxycholesterol (25-HC), followed by subsequent metabolism to 7α,25-dihydroxycholesterol (7α,25-diHC) and 7α,25-dihydroxycholest-4-en-3-one (7α,25-diHCO). Of these metabolites, 7α,25-diHCO was elevated in ALS serum (P<0.01, FIG. 3*d*). 7α-Hydroxycholesterol (7α-HC, FIG. 3*b*) and 7α-hydroxycholest-4-en-3-one (7α-HCO, FIG. 3*c*) are the first members of the neutral pathway of bile acid biosynthesis; however, neither oxysterol showed a difference in concentration between ALS, PLS, or control samples, and nor did 7β-hydroxycholesterol (7β-HC) or 7-oxocholesterol (7O-C). Conversely, (25R)26-hydroxycholesterol (26-HC), the first member of the extrahepatic part of the acidic pathway of bile acid biosynthesis, was decreased in ALS and PLS serum compared with controls (P<0.01, FIG. 3*e*), as was 3β-hydroxycholest-5-en-26-oic acid (3β-HCA) in ALS serum (P<0.05, FIG. 3*f*). The level of 26-HC and other metabolites was normalised to cholesterol to determine whether the observed differences were still maintained. When normalized to cholesterol the elevation in the concentration of 7α,25-diHCO was retained in ALS, as was a decrease in the concentration of 26-HC.

Example 3

Analysis of Sterols, Oxysterols, and Cholestenoic and Cholenoic Acids in CSF

As with serum, levels of cholesterol, 7-DHC (plus 8-DHC), and desmosterol (24-DHC) were measured in CSF from ALS patients (n=20; 15 male, 5 female, mean age 61) and controls (n=15; 12 male, 3 female, mean age 75). The concentrations of both desmosterol (P<0.05, FIG. 4A) and cholesterol (P<0.01, FIG. 4C) were found to be elevated in CSF from ALS patients. Because ALS is a neurodegenerative disease, it was speculated that, when cholesterol is released by neurons as they die, it would be metabolized by CYP46A1 to 24S-hydroxycholesterol (24S-HC) and by CYP27A1 to members of the acidic pathway of bile acid biosynthesis. Surprisingly, when normalized to cholesterol, 24S-HC concentration was found to be reduced (P<0.01, FIG. 5d) in CSF, as were members of the acidic pathway of bile acid biosynthesis. Intriguingly, concentrations of 7α-HC, 7α-HCO, 7β-HC, and 7O-C, which originate from the CYP7A1-initiated arm of the bile acid biosynthesis pathway and enter the CSF from the circulation, did not differ between ALS patients and controls (FIG. 5 A, B, C).

The level of 26-HC was not significantly lower in CSF from ALS patients (0.09±0.06 ng/μg cholesterol) compared with controls (0.13±0.07 ng/μg cholesterol), but its downstream metabolites 3β-HCA (P<0.01, FIG. 6A), 3β,7α-dihydroxycholest-5-en-26-oic acid (3β,7α-diHCA P<0.05, FIG. 6A), and 7α-hydroxy-3-oxocholest-4-en-26-oic acid (7αH,3O-CA; P<0.01, FIG. 6C) were all reduced in concentration (ng/μg cholesterol) in ALS CSF (FIG. 6).

Peroxisomal metabolites found in CSF include 7α,24-dihydroxy-3-oxocholest-4-en-26-oic acid (7α,24-diH,3O-CA FIG. 6E); 7α-hydroxy-3,24-bisoxocholest-4-en-26-oic acid (7αH,3,24-diO-CA, FIG. 6E), which is also observed as the decarboxylated dione; 7α-hydroxy-26-norcholest-4-ene-3,24-dione (7αH,26-nor-C-3,24-diO, FIG. 6F); and the oxidation product 7α-hydroxy-3-oxochol-4-en-24-oic acid (7αH,3O-Δ$^4$-BA). With the exception of the latter compound, all of the peroxisomal intermediates were decreased (P<0.05 or 0.01; ng/μl cholesterol) in CSF from ALS patients.

Levels of oxysterols present in cerebrospinal fluid in the population of ALS patients relative to a control group are summarised in table 2. ng/mL refers to absolute levels, "Normalised" to levels normalised to cholesterol.

Figure 1:
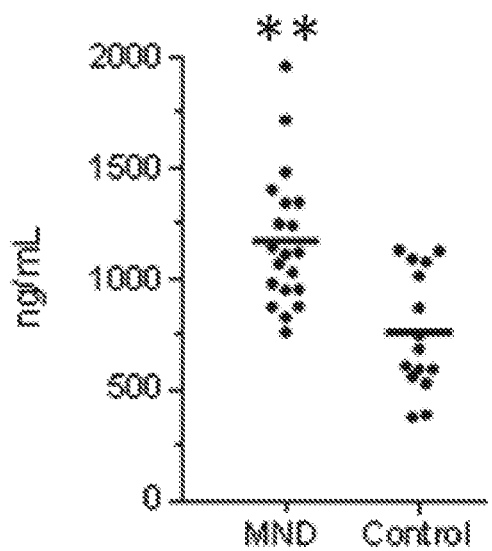
FIG. 1 is a graph showing the level of cholesterol (1) measured in cerebrospinal fluid in patients suffering from amyotrophic lateral sclerosis ("MND", left hand column) compared with that measured in a control population ("control", right hand column).

FIG. 1 shows the level of cholesterol (1) measured in cerebrospinal fluid in patients suffering from amyotrophic lateral sclerosis ("MND", left hand column) compared with that measured in a control population ("control", right hand column).

Figure 2:
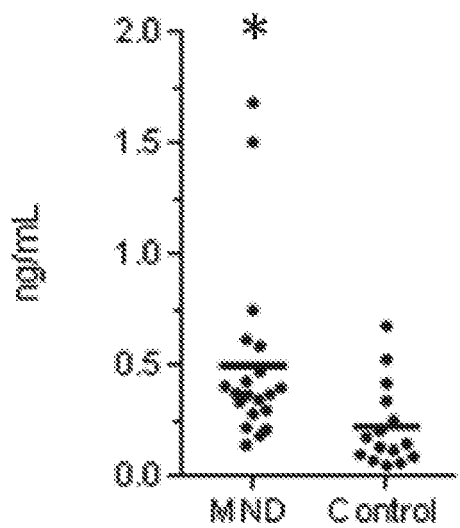
FIG. 2 is a graph showing the level of desmosterol (2) measured in cerebrospinal fluid in patients suffering from amyotrophic lateral sclerosis ("MND", left hand column) compared with that measured in a control population ("control", right hand column).

FIG. 2 is shows the level of desmosterol (2) measured in cerebrospinal fluid in patients suffering from amyotrophic lateral sclerosis ("MND", left hand column) compared with that measured in a control population ("control", right hand column).

The invention claimed is:

1. A method for determining whether a subject suspected of having amyotrophic lateral sclerosis (ALS) is afflicted with ALS, the method comprising:
   (a) obtaining a sample of a supernatant from centrifuged cerebrospinal fluid from the subject;
   (b) subjecting the sample to analysis to determine the concentration in the sample of at least one of a steroid selected from cholesterol (1), desmosterol (2), or combinations thereof, and optionally an additional oxysterol;
   (c) comparing the concentration of the at least one steroid present in the sample to a reference value of the at least one steroid obtained from a control population consisting of individuals not afflicted with ALS; and
   (d) diagnosing the subject as afflicted with ALS if the concentration of the at least one steroid from the subject is greater than the reference value.

TABLE 2

| | | CSF | | Plasma | | |
|---|---|---|---|---|---|---|
| Systematic Name | Abbreviation | ng/mL | Normalised | ng/mL | Normalised | FIG. |
| 3β,7α-dihydroxycholest-5-en-26-oic acid | 3β,7α-diHCA | | Reduced | | | 6b |
| 3β-hydroxycholest-5-en-26-oic acid | 3β-HCA | | Reduced | | Reduced | 6a 3f |
| 3β,7β-Dihydroxycholest-5-en-26-oic acid | 3β,7β-diHCA | | Reduced | | | 6d |
| 7α-hydroxy-3-oxocholest-4-en-26-oic acid | 7αH,3O-CA, | | Reduced | | | 6c |
| (25R)26-hydroxycholesterol, Cholest-5-ene-3β,24S-diol | 26-HC | | | Reduced | Reduced | 3e |
| | 24-S HC | | Reduced | | | 5d |
| 7α,25-Dihydroxycholest-4-en-3-one | 7α-25-diHCO | Reduced | Reduced | Increased | Increased | 5e |
| 7α,26-Dihydroxycholest-4-en-3-one | 7α-26-diHCO | Reduced | Reduced | | | 5f |
| 7α,24-Dihydroxy-3-oxocholest-4-en-26-oic acid | 7α,24-diH, 3O-CA | | Reduced | | | 6e |
| 7α-Hydroxy-26-nor-cholest-4-ene-3,24-dione | 7α-H,26-nor-C3,24-diO | | Reduced | | | 6f |
| 7α-Hydroxy-3,24-bisoxocholest-4-en-26-oic acid | 7αH,3,24-diO-CA | | Reduced | | | |
| 7α-Hydroxy-3-oxochol-4-en-24-oic acid | 7αH,3O-Δ$^4$-BA | Increased | | | | |

2. The method according to claim 1 wherein the additional oxysterol is selected from 3β,7α-dihydroxycholest-5-en-26-oic acid (3β,7α-diHCA),
3β-hydroxycholest-5-en-26-oic acid (3β-HCA),
3β,7β-Dihydroxycholest-5-en-26-oic acid (3β,7β-diHCA)
7α-hydroxy-3-oxocholest-4-en-26-oic acid (7αH,3O-CA)
(25R)26-hydroxycholesterol (26-HC)
Cholest-5-ene-3β,24S-diol (24-S HC)
7α,25-Dihydroxycholest-4-en-3-one (7α-25-diHCO)
7α,26-Dihydroxycholest-4-en-3-one (7α-26-diHCO)
7α,24-Dihydroxy-3-oxocholest-4-en-26-oic acid (7α,24-diH, 3O-CA)
7α-Hydroxy-26-nor-cholest-4-ene-3,24-dione (7α-H,26-nor-C3,24-diO)
7α-Hydroxy-3,24-bisoxocholest-4-en-26-oic acid (7αH, 3,24-diO-CA); and
7α-Hydroxy-3-oxochol-4-en-24-oic acid (7αH,3O-$\Delta^4$-BA).

3. The method according to claim 1 wherein the additional oxysterol is selected from 17α-hydroxy-3-oxocholest-4-enoic acid (7αH,3O-CA, (3)), 7α,(25R)26-dihydroxycholest-4-en-3-one, (7α,(25R)26-diHCO (4)) and combinations thereof.

4. The method according to claim 1 wherein the analysis comprises a chromatographic method.

5. The method according to claim 1, wherein the analysis comprises a mass spectrometry method.

6. The method according to claim 1 wherein the analysis is conducted using liquid chromatography-mass spectrometry (lc-ms).

7. The method according to claim 5 wherein the sample is reacted with a tagging agent prior to analysis.

8. The method according to claim 7 wherein the tagging agent is a hydrazine tagging agent.

9. The method according to claim 7 wherein the tagging agent is Girard reagent P.

10. The method according to claim 4 wherein a reference compound is included prior to analysis.

11. The method according to claim 1 wherein the at least one steroid is cholesterol (1).

12. The method according to claim 11 wherein the method of determining the level of cholesterol is selected from the Abell-Levy-Brodie-Kendall (ALBK) saponification method, the cholesterol ester hydrolase-cholesterol oxidase-peroxidase (CEH-CO-POD) chromogenic method, and an enzymatic procedure using NAD(P1)-specific cholesterol dehydrogenase (CDH).

13. The method according to claim 1 comprising the further steps of
(a) obtaining a sample of plasma from the subject;
(b) subjecting the plasma sample to analysis to determine the concentration in the sample of at least one of one oxysterol selected from 3β-hydroxycholest-5-en-26-oic acid (3β-HCA), (25R)26-hydroxycholesterol (26-HC), 7α-hydroxy-3-oxochol-4-enoic acid (7αH,3O-$\Delta^4$-BA, (5)), 7-oxocholesterol (7O-C, (6)) and 7α-hydroxycholest-4-en-3-one (7α-HCO, (7)) or combinations thereof;
(c) comparing the concentration of the at least one oxysterol present in the plasma sample to a reference value of the at least one oxysterol obtained from a control population consisting of individuals not afflicted with ALS; and
(d) diagnosing the subject as afflicted with ALS if the concentration of the at least one oxysterol present in the plasma sample from the subject is lower than the reference value.

14. The method according to claim 1 comprising the further steps of
(a) obtaining a sample of plasma from the subject;
(b) subjecting the plasma sample to analysis to determine the concentration in the sample of at least one of one oxysterol selected from 7α,25-Dihydroxycholest-4-en-3-one (7α-25-diHCO),
(c) comparing the concentration of the at least one oxysterol present in the plasma sample to a reference value of the at least one oxysterol obtained from a control population consisting of individuals not afflicted with ALS; and
(d) diagnosing the subject as afflicted with ALS if the concentration of the at least one oxysterol present in the plasma sample from the subject is higher than the reference value.

15. A method of identifying an agent for the treatment of ALS, the method comprising:
(a) administering a candidate agent to a non-human mammal model of ALS;
(b) obtaining a sample of a supernatant from centrifuged cerebrospinal fluid from the non-human mammal;
(c) subjecting the sample to analysis to determine the concentration in the sample of at least one of a steroid selected from cholesterol (1), desmosterol (2), or combinations thereof, and optionally an additional oxysterol;
(d) comparing the concentration of the at least one steroid present in the sample to a reference value of the at least one steroid obtained from a control population consisting of individuals not afflicted with ALS; and
(e) identifying the candidate agent as an agent for the treatment of ALS if the concentration of the at least one steroid from the subject is decreased compared to the value prior to administration.

16. A method for determining the responsiveness of a subject having amyotrophic lateral sclerosis (ALS) to treatment with at least one ALS therapy, the method comprising
(a) administering the at least one ALS therapy to a subject having ALS;
(b) obtaining a sample of a supernatant from centrifuged cerebrospinal fluid from the subject;
(c) subjecting the sample to analysis to determine the concentration in the sample of at least one of a steroid selected from cholesterol (1), desmosterol (2), or combinations thereof, and optionally an additional oxysterol;
(d) comparing the concentration of the at least one steroid present in the sample to the level of the same steroid or steroids prior to administration of the therapy;
wherein an increase in the concentration of the at least one steroid is indicative that the subject is responsive or is likely to respond to the therapy.

17. A method of identifying a subject having amyotrophic lateral sclerosis (ALS) as suitable for treatment with at least one ALS therapy comprising the steps of
(a) obtaining a sample of a supernatant from centrifuged cerebrospinal fluid from the subject;
(b) subjecting the sample to analysis to determine the concentration in the sample of at least one of a steroid selected from cholesterol (1), desmosterol (2), or combinations thereof, and optionally an additional oxysterol;

(c) comparing the concentration of the at least one steroid present in the sample to a reference value of the at least one steroid obtained from a control population consisting of individuals not afflicted with ALS; and (d) diagnosing the subject as suitable for treatment with the therapy if the concentration of the at least one steroid from the subject is greater than the reference value.

18. The method according to claim 15 wherein the at least one steroid comprises cholesterol.

19. The method according to claim 15 wherein the therapy includes administration of at least one of edvaradone and riluzole.

\* \* \* \* \*